US010427996B2

(12) United States Patent
Tavares et al.

(10) Patent No.: US 10,427,996 B2
(45) Date of Patent: Oct. 1, 2019

(54) FERMENTATION HYDROCARBON GAS PRODUCTS SEPARATION VIA MEMBRANE

(71) Applicant: Braskem S.A., Camacari, BA (BR)

(72) Inventors: Luiz Felipe de Souza Tavares, Rio de Janeiro (BR); Bruno Maia Moreira, Rio de Janeiro (BR); Paulo Luiz de Andrade Coutinho, Sao Paulo (BR); Roberto Werneck do Carmo, Sao Paulo (BR)

(73) Assignee: Braskem S.A., Camacari (BR)

( * ) Notice: Subject to any disclaimer, the term of this patent is extended or adjusted under 35 U.S.C. 154(b) by 60 days.

(21) Appl. No.: 15/100,783

(22) PCT Filed: Dec. 2, 2014

(86) PCT No.: PCT/BR2014/050024
§ 371 (c)(1),
(2) Date: Jun. 1, 2016

(87) PCT Pub. No.: WO2015/081406
PCT Pub. Date: Jun. 11, 2015

(65) Prior Publication Data
US 2016/0304416 A1 Oct. 20, 2016

Related U.S. Application Data

(60) Provisional application No. 61/910,650, filed on Dec. 2, 2013.

(51) Int. Cl.
*C07C 7/12* (2006.01)
*C07C 7/144* (2006.01)
(Continued)

(52) U.S. Cl.
CPC .............. *C07C 7/144* (2013.01); *B01D 11/04* (2013.01); *B01D 53/04* (2013.01); *B01D 53/22* (2013.01); *B01D 53/226* (2013.01); *B01D 53/228* (2013.01); *B01D 71/10* (2013.01); *B01D 71/48* (2013.01); *B01D 71/50* (2013.01); *B01D 71/52* (2013.01); *B01D 71/56* (2013.01); *B01D 71/64* (2013.01); *B01D 71/68* (2013.01); *C07C 7/005* (2013.01); *C07C 7/04* (2013.01); *C07C 7/11* (2013.01); *C07C 7/12* (2013.01); *F25J 3/08* (2013.01); *B01D 2253/108* (2013.01); *B01D 2253/116* (2013.01); *B01D 2256/24* (2013.01); *B01D 2257/104* (2013.01); *B01D 2257/40* (2013.01); *B01D 2257/504* (2013.01);
(Continued)

(58) Field of Classification Search
CPC ......... C07C 7/144; C07C 7/005; C07C 11/04; C07C 11/06; C07C 11/08; C07C 11/09; C07C 11/167; C07C 11/18; C07C 7/04; C07C 7/11; C07C 7/12; B01D 53/228; B01D 11/04; B01D 2253/108; B01D 53/04; B01D 53/22; B01D 53/226; B01D 71/10; B01D 71/48; B01D 71/50; B01D 71/52; B01D 71/56; B01D 71/64; B01D 71/68
USPC ........................................ 585/810, 833, 809
See application file for complete search history.

(56) References Cited

U.S. PATENT DOCUMENTS

| 5,409,524 A * | 4/1995 | Jensvold .............. B01D 67/009 55/DIG. 5 |
| 5,503,750 A | 4/1996 | Russo, Jr. et al. |

(Continued)

FOREIGN PATENT DOCUMENTS

| DE | 10 2007 054 150 A1 | 5/2009 |
| FR | 2 974 311 A1 | 10/2012 |

(Continued)

OTHER PUBLICATIONS

"Module" definition. Dictionary.com. Accessed May 24, 2017.*
WO 9716399—English Machine Translation obtained Feb. 7, 2018.*

*Primary Examiner* — Sharon Pregler
(74) *Attorney, Agent, or Firm* — Duane Morris LLP (57) ABSTRACT

Disclosed herein is a process for separation and purification of a fermentation gas product from a fermenter off-gas containing a fermentation product, volatile impurities, bio-product impurities and water, based on a membrane system. In one preferred embodiment of the present invention, the process of separating and purifying a fermentation product from a fermenter off-gas, containing the fermentation product, volatile impurities, bio-byproduct impurities and water, comprises the steps of: (a) compressing the fermenter off-gas and feeding it into a membrane module, and (b) selectively permeating the volatile impurities, bio-byproduct impurities and water through the membrane, resulting in a product rich retentate stream. The fermentation gas product is separated from the fermenter off-gas in a single membrane stage to produce a purified retentate stream. In accordance with this embodiment of the invention, the fermenter off-gas (2), comprising the fermentation gas product, volatile impurities, bio-byproduct impurities and water, passes through a blower (201) that transports it to a gas holder (202), in order to smooth the process fluctuations. Stream (11) exits the gas holder (202) and is compressed in a multi-stage compressor (203), from which bio-byproduct and water are removed through stream (4). The compressed stream (12) enters the membrane module (204), which permeates the volatile impurities, disposing them in stream (13). The process may be still conducted in a 2-stage membrane system in accordance with the present invention.

30 Claims, 5 Drawing Sheets

(51) Int. Cl.
*B01D 53/22* (2006.01)
*C07C 7/00* (2006.01)
*B01D 11/04* (2006.01)
*B01D 53/04* (2006.01)
*B01D 71/10* (2006.01)
*B01D 71/48* (2006.01)
*B01D 71/50* (2006.01)
*B01D 71/52* (2006.01)
*B01D 71/56* (2006.01)
*B01D 71/64* (2006.01)
*B01D 71/68* (2006.01)
*C07C 7/04* (2006.01)
*C07C 7/11* (2006.01)
*F25J 3/08* (2006.01)

(52) U.S. Cl.
CPC ...... *B01D 2257/80* (2013.01); *B01D 2258/05* (2013.01); *B01D 2317/022* (2013.01); *Y02C 10/10* (2013.01); *Y02P 20/152* (2015.11); *Y02P 20/51* (2015.11)

(56) References Cited

U.S. PATENT DOCUMENTS

| | | | |
|---|---|---|---|
| 8,324,442 B2 | 12/2012 | McPhee | |
| 8,569,562 B2 | 10/2013 | Feher et al. | |
| 2006/0247399 A1* | 11/2006 | McConville | B01J 31/1815 526/170 |
| 2011/0028759 A1 | 2/2011 | Lum et al. | |
| 2011/0046422 A1* | 2/2011 | McAuliffe | C07C 9/14 585/16 |
| 2011/0178261 A1* | 7/2011 | Feher | B01D 11/0426 526/340.2 |
| 2012/0137878 A1* | 6/2012 | Wijmans | B01D 53/22 95/45 |
| 2013/0225884 A1* | 8/2013 | Weinberger | F25J 3/0219 585/16 |
| 2015/0336046 A1* | 11/2015 | Ungerank | B01D 53/22 95/8 |

FOREIGN PATENT DOCUMENTS

| | | | | |
|---|---|---|---|---|
| JP | WO 9716399 A1 * | 5/1997 | | B01D 53/226 |
| WO | 01/92555 A1 | 12/2001 | | |

* cited by examiner

FERMENTATION HYDROCARBON GAS PRODUCTS SEPARATION VIA MEMBRANE

TECHNICAL FIELD

The present invention relates to the field of fermentation hydrocarbon gas product purification. More specifically, the present invention describes a process for separation and purification of a hydrocarbon gas product, produced by fermentation, based on a membrane system.

BACKGROUND ART

The production of hydrocarbon gas products via anaerobic fermentation often results in a fermenter off-gas containing various amounts of impurities as part of the fermentation process (e.g. water vapor from the fermentation media, carbon dioxide as a respiration product, as well as other organic bio-byproducts). In aerobic fermentation the fermenter off-gas also contains nitrogen and oxygen impurities from aeration.

While a wide variety of commercial products can be manufactured by fermentation processes, some efforts have been made on development of purification of fermentation hydrocarbon products from fermenter off-gas streams.

U.S. Pat. No. 8,324,442 discloses purification methods for fermentation derived gaseous isoprene compositions using chillers and flash drums in order to obtain a liquid isoprene enriched composition at temperatures below −35° C. In some embodiments, the method further comprises extracting hydrocarbon impurities at some point of the purification process using a modified zeolite membrane and/or molecular sieve wherein the modified zeolite and/or molecular sieves selectively adsorb isoprene and not the other hydrocarbons in the composition or vice versa (adsorb other hydrocarbons in the composition and not isoprene).

U.S. Pat. No. 8,569,562 discloses methods and apparatus for the purification of a bioisoprene composition from fermenter off-gas based on solvent extraction comprising one or more columns to remove volatile and/or bio-byproduct impurities resulting from fermentation.

The present invention provides a new fermentation hydrocarbon gas product separation and purification process based on a membrane system. In one aspect, the present invention provides a fermenter off-gas separation and purification process in order to obtain a fermentation product rich gaseous stream with at least 70% wt of the fermentation hydrocarbon product without working under low temperatures or using solvent.

SUMARY OF THE INVENTION

The present invention refers to a process for separating impurities from the gaseous product from a fermentation process to produce purified fermentation derived hydrocarbon.

The invention comprises the steps of: (a) contacting a membrane selectively permeable to the impurities with a gaseous mixture comprising the fermentation hydrocarbon gas product, and (b) permeating these impurities through the membrane, resulting in a retentate stream rich in fermentation hydrocarbon gas product.

In a first embodiment, the separation is conducted in a single membrane step, with the feed being the fermenter off-gas, the permeate comprising carbon dioxide and other impurities and the retentate comprising the fermentation hydrocarbon gas product rich stream.

In a second preferred embodiment of the present invention, two membranes stages are used in series, where the permeate of the first membrane stage is fed in a second membrane stage in order to reduce product losses by recycling part of the impurities stream.

In a third embodiment of the present invention, two membranes stages are used in series, where the retentate of the first membrane is fed in a second membrane stage.

Other embodiments can be adopted with multiple membrane and compression stages, which are not intended to limit the scope or underlying principles of the invention in any way.

DETAILED DESCRIPTION OF THE INVENTION

The present invention is a process for separating impurities from the hydrocarbon gaseous product from a fermentation process to produce a fermentation hydrocarbon gas product using membranes.

The "gaseous stream" comprises a fermenter off-gas comprising the fermentation hydrocarbon gas product, volatiles impurities, bio-byproduct impurities and water.

The "fermentation hydrocarbon gas product" (or fermentation product) comprises a hydrocarbon gaseous compound produced in a fermentation process. Preferably, the fermentation hydrocarbon gas product is selected from the group consisted of ethylene, propylene, isobutylene, 1-butene, butadiene and isoprene. More preferably, the fermentation hydrocarbon gas is butadiene.

The fermentation hydrocarbon gas product can be obtained by aerobic or anaerobic fermentation process. When the fermentation is anaerobic, the "volatile impurities" can comprise $H_2O$ and $CO_2$, wherein the volatile impurities comprises about 30 to about 80 mol % $CO_2$, and about 1 to about 20 mol % $H_2O$. When the fermentation is aerobic, the volatile impurities can comprise $H_2O$, $CO_2$, $N_2$ and $O_2$, wherein the volatile impurity comprises about 5 to about 70 mol % $CO_2$, about 1 to about 20 mol % $H_2O$, about 40 to about 95 mol % $N_2$, and about 0.5 to about 15 mol % $O_2$.

The bio-byproduct impurity comprises a polar impurity that can be selected from the group consisting of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5 -trimethyl-pyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl- 1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatetraene, (E)-7,11-dimethyl-3-methylene-1,6,10-dodecatriene, 3-hexen-1-ol, 3-hexen-1-yl acetate, lmonene, geraniol (trans-3,7-dimethyl-2,6-octadien-1-ol), and citronellol (3,7-dimethyl-6-octen-1-ol).

The term "membrane" as used herein is intended to encompass a wide variety of possible configurations known in the prior art. For example, the membrane may be used as a flat film, tubular film or hollow fiber.

The membrane material can be based on a wide range of polymers, such as polyacetylene, poly(ethylene oxide), polysulfone, polyethersulfone, styrenic polymers and copolymers, polycarbonates, cellulosic polymers, polyamides, polyimides, polyethers, polyarylates, poly(arylene ether), poly(arylene oxide), poly(phenylene oxide), poly(pyrrolone), polyurethanes, polyesters, polyacrylates, polysulfides, polyolefins, polyvinyls and polyvinyl esters. Mixture of these polymers can be used as well.

Other subsequent purification procedures, such as cryogenic distillation, organic solvent extraction or by using an adsorption system, may also be adopted. When a solvent extraction is performed, the solvent can be selected from the group comprising C11 through C13 hydrocarbons.

In a first preferred embodiment of the present invention, the process of separating and purifying a fermentation hydrocarbon product from a fermenter off-gas, containing the fermentation hydrocarbon product, volatile impurity, bio-byproduct impurity and water, comprises the steps of: (a) compressing the fermenter off-gas and feeding it into a membrane module, and (b) selectively permeating the volatile impurity, bio-byproduct impurity and water through the membrane, resulting in a hydrocarbon product rich retentate stream. This embodiment is shown of FIG. 1 wherein the fermentation hydrocarbon gas product is separated from the fermenter off-gas in a single membrane stage to produce purity purified retentate stream.

Figure 1:
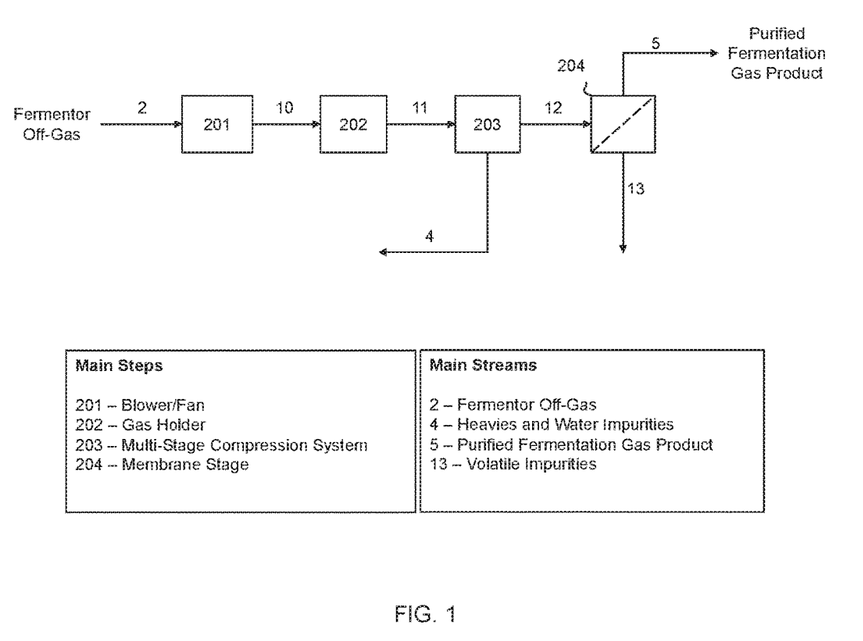
FIG. 1 is a single stage membrane for fermentation gas product separation.

In accordance with this first embodiment of the invention and referring to FIG. 1, the fermenter off-gas 2, comprising the fermentation hydrocarbon gas product, volatile impurities, bio-byproduct impurities and water, passes through a blower 201 that transports it via stream 10 to a gas holder 202, in order to smooth the process fluctuations.

Stream 11 exits the gas holder 202 and is compressed in a multi-stage compressor 203, from which bio-byproduct and water are removed through stream 4. The compressed stream 12 enters the membrane module 204, which permeates the volatile impurities, disposing them in stream 13.

The retentate stream 5 may pass through further purification processes (not shown in the FIG. 1), which can comprise an adsorption system, cryogenic distillation or extraction via solvent or a combination thereof. The purity of the product stream 5 is about 70% wt or greater.

In a second preferred embodiment of the present invention, the process of separation and purifying a fermentation product from a fermenter off-gas, containing the fermentation hydrocarbon product, volatile impurity, bio-byproduct impurity and water, comprises the steps of: (a) compressing the fermenter off-gas and feeding it into a first membrane stage, (b) selectively permeating the volatile impurity, bio-byproduct impurity and water through the first membrane stage and obtaining a fermentation hydrocarbon product rich retentate stream, (c) compressing the permeate stream from the first membrane stage, (d) selectively permeating the volatile impurity, bio-byproduct impurities and water through the second membrane stage and, (e) recycling the retentate stream from the second membrane stage to the first membrane stage.

Figure 2:
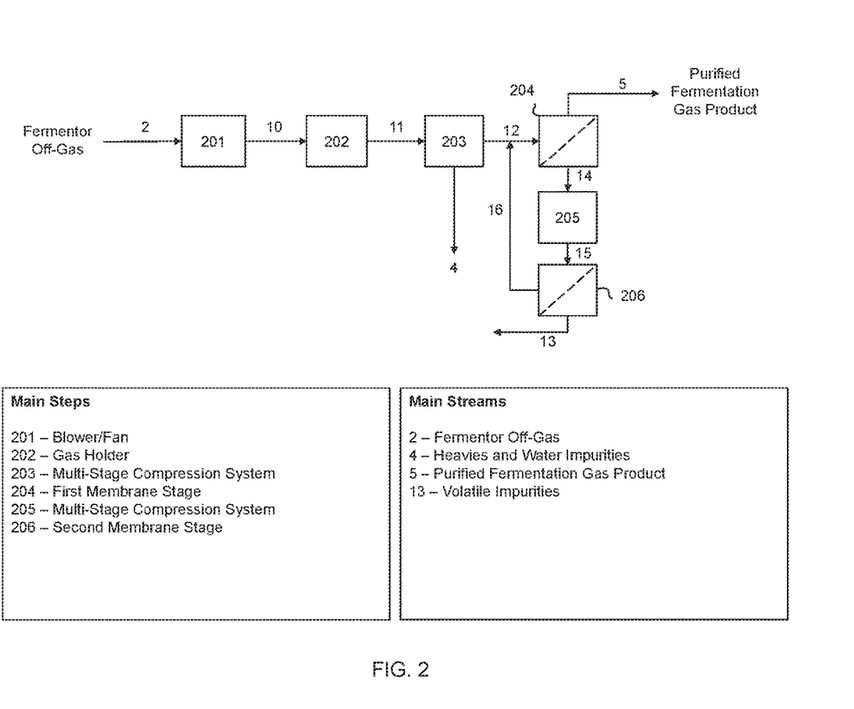
FIG. 2 is a fermentation gas product separation via 2-stage membranes with product being the retentate from the first membrane step.

FIG. 2 illustrates the second preferred embodiment of the invention, wherein the fermentation gas product is separated from the fermenter off-gas in a 2-stage membrane system to produce purified fermentation gas product as the retentate stream from the first membrane stage.

The fermenter off-gas 2, comprising fermentation hydrocarbon gas product, volatile impurities, bio-byproduct impurities and water, passes through a blower 201 and is fed via stream 10 to a gas holder 202, to smooth process fluctuations.

Stream 11 exits the gas holder 202 and is compressed in a multi-stage compressor 203, from which bio-byproduct and water are removed through stream 4. The compressed stream 12 enters the first membrane stage 204, which permeates the volatile impurities. The permeate stream 14 is then compressed in the multi-stage compressor 205 and sent through stream 15 to the second membrane stage 206. Volatile impurities are permeated by the membrane and disposed by stream 13. Stream 16, still containing the fermentation hydrocarbon gas product, passes through a compressor (not shown) and is recycled to membrane 204.

This membrane configuration is capable of reaching a high purity fermentation hydrocarbon product (≥90 wt %) in stream 5. The stream 5 may pass through further purification processes (not shown in the figure), which can comprise an adsorption system, cryogenic distillation or extraction via solvent or combination thereof. The purity of the product retentate stream 5 is about 90 wt % or greater.

In a third preferred embodiment of the present invention, the process of separation and purifying a fermentation hydrocarbon product from a fermenter off-gas, containing the fermentation hydrocarbon product, volatile impurity, bio-byproduct impurity and water, comprises the steps of: (a) compressing the fermenter off-gas and feeding it into a first membrane stage, (b) selectively permeating the volatile impurity, bio-byproduct impurity and water through the first membrane stage and obtaining a fermentation hydrocarbon product rich retentate stream, (c) selectively permeating the retentate through the second membrane stage and, (d) recycling the permeate stream from the second membrane stage to the first membrane stage.

Figure 3:
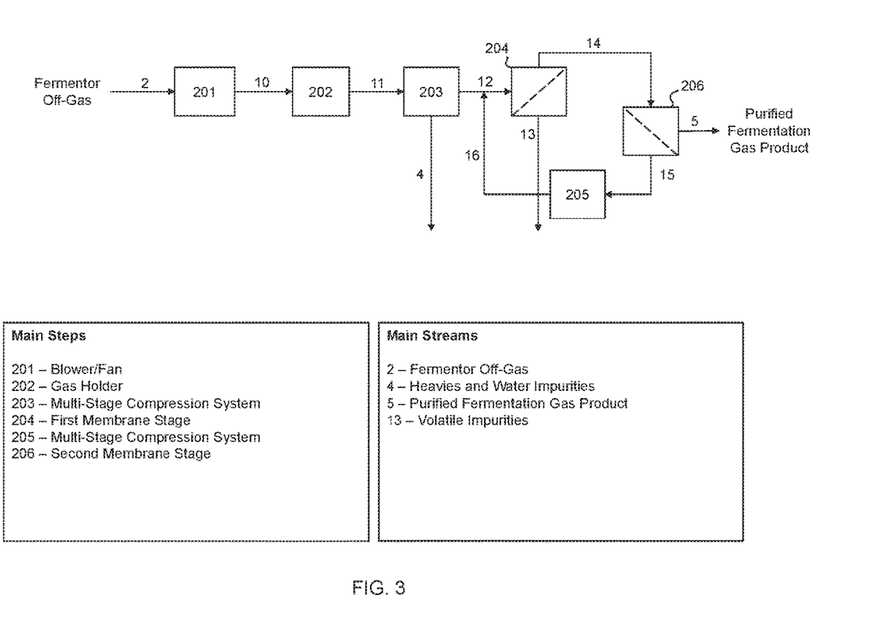
FIG. 3 is a fermentation gas product separation via 2-stage membranes with product being the retentate from the second membrane step.

FIG. 3 illustrates the third embodiment of the invention, wherein the fermentation hydrocarbon gas product is separated from the fermenter off-gas in a 2-stage membrane system, with recycle, to produce high purity fermentation hydrocarbon product in the retentate stream from the second membrane stage.

The fermenter off-gas 2, comprising fermentation hydrocarbon gas product, volatile impurities, bio-byproduct impurities and water, passes through a blower 201 and is fed via stream 10 to a gas holder 202 to smooth the process fluctuations.

Stream 11 exits the gas holder 202 and is compressed in a multi-stage compressor 203, from which bio-byproduct and water are removed through stream 4. The compressed stream 12 enters the first membrane stage 204, which permeates the volatile impurities, disposing them through stream 13. The retentate stream 14 is sent to the second membrane stage 206. The permeate stream 15 then passes through the multi-stage compressor 205 and is recycled to membrane 204.

The retentate 5 may pass through further purification processes (not shown in the FIG. 3), which can comprise an adsorption system, cryogenic distillation or extraction via solvent or combination thereof, producing the high purity fermentation gas product in stream 5.

Figure 4:
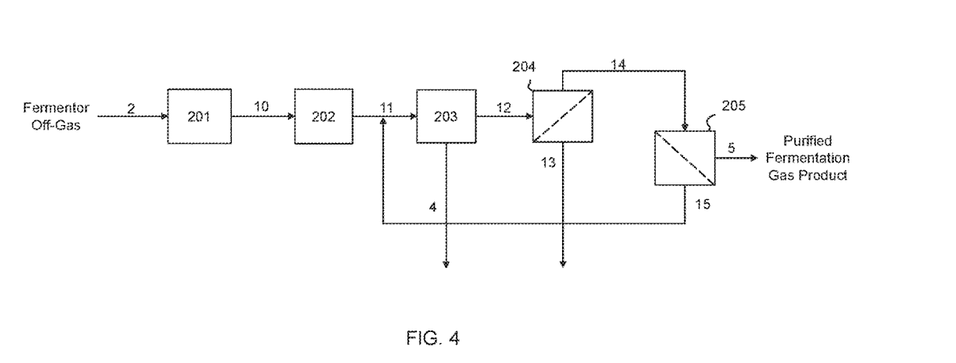
FIG. 4 is a fermentation gas product separation via 2-stage membranes with product being the retentate from the second membrane step, alternate embodiment.
Figure 5:
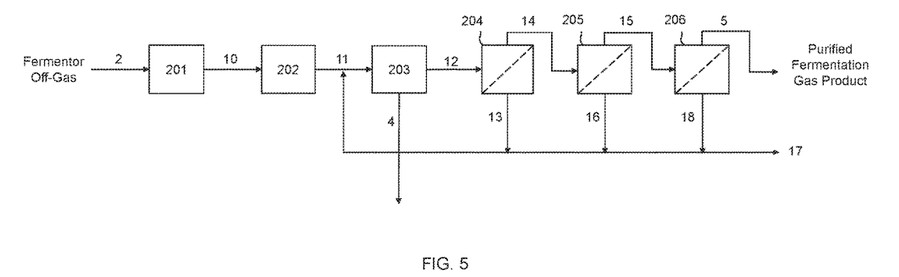
FIG. 5 is a fermentation gas product separation with 3 membranes ordered in series and with recycle.

FIG. 4 and FIG. 5 represent other possible configurations of the invention, in which 201 is a blower, 10 is a stream, 202 is a gas holder, 203 is a multi-stage compression stage and 204, 205 and 206 (stream 18 exiting stage 206) are membrane stages. Other configurations different from the examples shown can be adopted with multiple membrane and compression stages, which are not intended to limit the scope or underlying principles of the invention in any way.

As the retentate stream passes from one membrane to another, it will contain higher purity of the product than it had before and the permeate stream, higher impurity percentage.

The number of membrane modules to compose the system depends on the final purity required and the maximum losses allowed.

Compressors can be used to ensure the differential pressure at any membrane step. The compressor outlet pressure is about 5 to about 25 bar, preferentially about 8 to about 15 bar. The membrane permeate pressure is about 0.1 to about 10 bar, preferentially about 1 to about 5 bar.

EXAMPLE

Butadiene (fermentation gas product) is separated from the fermenter off-gas comprising 31.9% wt of butadiene, 61.9% wt of $CO_2$, 5 ppm wt/wt of 1,4-butanediol, and 6.3% wt of water in a 2-stage membrane system, according (FIG. 2) to produce purified butadiene (99.99% wt).

The fermenter off-gas 2 (temperature=37.5° C. and p=1 atm), comprising butadiene, $CO_2$, 1,4-butanediol and water, passes through a blower 201 and is fed to a gas holder 202, to smooth process fluctuations. Stream 11 exits the gas holder 202 and is compressed in a multi-stage compressor 203, from which 1,4-butanediol and water are removed through stream 4. The compressed stream 12 (35.9% wt of butadiene, 62.1% wt of $CO_2$ and 2.1% wt of water), enters the first membrane stage 204 at T=96.5° C. and p=10 bar, which permeates the volatile impurities. The permeate stream 14 is then compressed in the multi-stage compressor 205 and sent through stream 15 to the second membrane stage 206 at T=116.2° C. and p=10 bar. Volatile impurities are permeated by the membrane and disposed by stream 13. Stream 16, still containing the butadiene, passes through a compressor (not shown) and is recycled to membrane 204.

In order to obtain a butadiene stream with 99.99% wt of purity, with a membrane with $CO_2$ permeability of 65.5 Barrer and Butadiene permeability of 4.2 Barrer leading to a $CO_2$/Butadiene selectivity of 15.6, the membrane area required is 46,000 $m^2$ for the first stage and 2,640 $m^2$ for the second stage. Selecting a membrane with $CO_2$ permeability of 210 Barrer and Butadiene permeability of 4.2 Barrer leading to a $CO_2$/Butadiene selectivity of 50, the membrane area required is 5,000 $m^2$ for the first stage and 1,800 $m^2$ for the second stage.

In order to obtain a butadiene stream with 90,00% wt of purity, with a membrane with $CO_2$ permeability of 65.5 Barrer and Butadiene permeability of 4.2 Barrer leading to a $CO_2$/Butadiene selectivity of 15.6, the membrane area required is 11,680 $m^2$ for the first stage and 2,200 $m^2$ for the second stage. Selecting a membrane with $CO_2$ permeability of 210 Barrer and Butadiene permeability of 4.2 Barrer leading to a $CO_2$/Butadiene selectivity of 50, the membrane area required is 1,600 $m^2$ for the first stage and 800 $m^2$ for the second stage.

INDUSTRIAL APPLICABILITY

The present invention pertains fundamentally to the field of separation and purification of purification of a hydrocarbon gas product, produced by fermentation.

What is claimed is:

1. A method of separating and purifying a fermentation product directly from a fermenter off-gas containing the fermentation product, volatile impurities and bio-byproduct impurities, comprising the steps of: (a) compressing the fermenter off-gas to produce a compressed off-gas on a multi-stage compressor system wherein the bio-byproduct impurities and water are removed, and feeding the compressed off-gas into at least one membrane module comprising a membrane, and (b) selectively permeating the volatile impurities through the membrane, resulting in a retentate stream rich in the fermentation product.

2. The method of claim 1, wherein the fermentation product comprises a compound selected from the group consisting of ethylene, propylene, isobutylene, 1-butene, 1,3-butadiene and isoprene.

3. The method of claim 1, wherein the volatile impurities comprise one or more compounds selected from the group consisting of $H_2O$, $CO_2$, $N_2$ and $O_2$.

4. The method of claim 3, wherein the volatile impurities comprise about 30 to about 80 mol % $CO_2$, and about 1 to about 20 mol % $H_2O$.

5. The method of claim 3, wherein the volatile impurities comprise about 5 to about 70 mol % $CO_2$, about 1 to about 20 mol % $H_2O$, about 40 to about 95 mol % $N_2$, and about 0.5 to about 15 mol % $O_2$.

6. The method of claim 1, wherein the bio-byproduct impurities comprise a polar impurity.

7. The method of claim 6, wherein the bio-byproduct impurities comprise a compound selected from the group consisting of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol, 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal,butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3 ,7,11-trimethyl-1,3,6,10-dodecatraene, (E)-7,11-dimethyl-3-methylene-1,6,10-dodecatriene, 3-hexen-1-ol, 3-hexen-1-yl acetate, limonene, geraniol (trans-3,7-dimethyl-2,6-octadien-1-ol), and citronellol (3,7-dimethyl-6-octen-1-ol).

8. The method of claim 1, wherein the membrane module comprises a membrane material selected from the group consisting of polyacetylene, poly(ethylene oxide), polysulfone, polyethersulfone, styrenic polymers and copolymers, polycarbonates, cellulosic polymers, polyamides, polyimides, polyethers, polyarylates, poly(arylene ether), poly(arylene oxide), poly(phenylene oxide), poly(pyrrolone), polyurethanes, polyesters, polyacrylates, polysulfides, polyolefins, polyvinyls, polyvinyl esters, and mixtures thereof.

9. The method of claim 1, wherein said compressing the fermenter off-gas takes place in a multi-stage compressor system operated at a compressor outlet pressure of about 5 to about 25 bar.

10. The method of claim 1, wherein the volatile impurities are permeated through the membrane at a pressure of about 0.1 to about 10 bar.

11. The method of claim 1, wherein the purity of the retentate stream rich in the fermentation product is 70 wt % or greater.

12. The method of claim 11, wherein the retentate stream rich in the fermentation product is further purified with an adsorption system.

13. The method of claim 11, wherein the retentate stream rich in the fermentation product is further purified with a cryogenic distillation system.

14. The method of claim 11, wherein the retentate stream rich in the fermentation product is further purified with a solvent extraction system.

15. The method of claim 14, wherein the solvent extraction system comprises a solvent, and the solvent comprises a hydrocarbon selected from the group consisting of $C_{11}$ through $C_{13}$ hydrocarbons.

16. A method of separating and purifying a fermentation product directly from a fermenter off-gas containing the fermentation product, volatile impurities and bio-byproduct impurities, comprising the steps of: (a) compressing the fermenter off-gas on a multi-stage compressor system wherein the bio-byproduct impurities and water are removed, and feeding the compressed off-gas into a first membrane stage, (b) selectively permeating the volatile impurities through the first membrane stage and obtaining a fermentation product rich retentate stream, (c) compressing a permeate stream from the first membrane stage on a multi-stage compressor system, (d) selectively permeating the volatile impurities through a second membrane stage comprising a membrane to produce a second retentate stream and, (e) recycling the retentate stream from the second membrane stage to the first membrane stage.

17. The method of claim 16, wherein the fermentation product comprises a compound selected from the group consisting of ethylene, propylene, isobutylene, 1-butene, 1,3- butadiene and isoprene.

18. The method of claim 16, wherein the volatile impurities comprise one or more compounds selected from the group consisting of $H_2O$, $CO_2$, $N_2$ and $O_2$.

19. The method of claim 18, wherein the volatile impurities comprise about 30 to about 80 mol % $CO_2$, and about 1 to about 20 mol % $H_2O$.

20. The method of claim 18, wherein the volatile impurities comprise about 5 to about 70 mol % $CO_2$, about 1 to about 20 mol % $H_2O$, about 40 to about 95 mol % $N_2$, and about 0.5 to about 15 mol % $O_2$.

21. The method of claim 16, wherein the bio-byproduct impurities comprise a polar impurity.

22. The method of claim 21, wherein the bio-byproduct impurities comprise one or more compounds selected from the group consisting of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol, 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatetraene, (E)-7,11-dimethyl-3-methylene-1,6,10-dodecatriene, 3-hexen-1-ol , 3-hexen-1-yl acetate, limonene, geraniol (trans-3,7-dimethyl-2,6-octadien-1-ol), and citronellol (3,7-dimethyl-6-octen-1-ol).

23. The method of claim 16, wherein the first membrane stage or the second membrane stage comprises a membrane material selected from the group consisting of polyacetylene, poly(ethylene oxide), polysulfone, polyethersulfone, styrenic polymers and copolymers, polycarbonates, cellulosic polymers, polyamides, polyimides, polyethers, polyarylates, poly(arylene ether), poly(arylene oxide), poly (phenylene oxide), poly(pyrrolone), polyurethanes, polyesters, polyacrylates, polysulfides, polyolefins, polyvinyls, polyvinyl esters, and mixtures thereof.

24. The method of claim 16, wherein said compressing the permeate stream from the first membrane stage on a multi-stage compressor system is performed at a compressor outlet pressure of about 5 to about 25 bar.

25. The method of claim 16, wherein the volatile impurities are permeated through the second membrane stage at a pressure of about 0.1 to about 10 bar.

26. The method of claim 16, wherein the purity of the fermentation product rich retentate stream is 90 wt % or greater.

27. The method of claim 26, wherein the fermentation product rich retentate stream is further purified with a cryogenic distillation system.

28. The method of claim 26, wherein the fermentation product rich retentate stream is further purified with a solvent extraction system.

29. The method of claim 28, wherein the solvent extraction system comprises a solvent, and the solvent comprises a hydrocarbon selected from the group consisting of $C_{11}$ through $C_{13}$ hydrocarbons.

30. The method of claim 16, wherein the fermentation product rich retentate stream is further purified with an adsorption system.

\* \* \* \* \*